US00PP26678P2

(12) United States Plant Patent
Kordes

(10) Patent No.: US PP26,678 P2
(45) Date of Patent: May 3, 2016

(54) GRANDIFLORA ROSE PLANT NAMED 'KORFRE0015'

(50) Latin Name: *Rosa hybrida*
Varietal Denomination: KORfre0015

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes Sohne Rosenschulen GmbH & Co. KG, Offenseth-Sparrieshoop (DE)

( * ) Notice: Subject to any disclaimer, the term of this patent is extended or adjusted under 35 U.S.C. 154(b) by 129 days.

(21) Appl. No.: 14/121,058

(22) Filed: Jul. 25, 2014

(51) Int. Cl.
*A01H 5/02* (2006.01)

(52) U.S. Cl.
USPC ..... Plt./134

(58) Field of Classification Search
USPC ..... Plt./101, 130, 134
See application file for complete search history.

*Primary Examiner* — Susan McCormick Ewoldt

(57) ABSTRACT

A new and distinct variety of rose with long lasting, novel lemon-yellow flowers, and attractive foliage with good disease resistance. It exhibits upright growth with abundant flowers. The new variety propagates well by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORfre0015'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2001. The crossing was between an un-named seedling, the seed parent, and another un-named seedling, the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORfre0015'.

SUMMARY OF THE INVENTION

The new rose plant may be distinguished from its seed parent, an un-named seedling, by the following combination of characteristics:

1. 'KORfre0015' has lemon yellow flowers, whereas the un-named seedling has amber yellow flowers.
2. 'KORfre0015' has medium-sized flowers, whereas the un-named seedling has large flowers.

The new rose plant may be distinguished from its pollen parent, an un-named seedling, by the following combination of characteristics:

1. 'KORfre0015' has lemon yellow flowers, whereas the un-named seedling has orange flowers.
2. 'KORfre0015' has an upright growth habit, whereas the un-named seedling has a spreading growth habit.

The objective of the hybridization was to create a new and distinct rose plant with unique qualities, such as:

1. Uniform growth and flowering;
2. Abundant attractive, recurrent flowers which can be used in the commercial cut flower trade;
3. Attractive and abundant foliage; and
4. Resistance to diseases encountered in commercial flower culture.

This combination of qualities is not present in prior rose cultivars known to the inventor. These objectives have been substantially achieved and in that distinguish 'KORfre0015' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORfre0015' was selected in 2007 from the seedling beds to be asexually propagated for further evaluation. The first asexual propagation of 'KORfre0015' was done by budding in 2009 at the inventor's nursery in Offenseth-Sparrieshoop, Germany.

These initial and other subsequent propagations conducted in controlled environments demonstrate that 'KORfre0015' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORfre0015'.

DETAILED BOTANICAL DESCRIPTION

The following is a description of 'KORfre0015', as observed growing in June 2014 in a nursery in Jackson County, Oreg. on plants of 4 years of age. Color references are made using The Royal Horticultural Society (London, England) Colour Chart, 2001 except where common terms of color are used.

For a comparison, several physical characteristics of the rose variety 'KORtiglo', a rose variety from the same inventor described and illustrated in U.S. Plant Pat. No. 19,385 and issued on Oct. 28, 2008 are compared to 'KORfre0015' in Chart 1.

CHART 1

| Characteristic | 'KORfre0015' | 'KORtiglo' |
|---|---|---|
| General tonality, open flower. | Yellow Group 11A. | Yellow-Orange Group 20C. |
| Open flower diameter. | 70 mm. | 100-120 mm. |
| Fragrance. | Strong fragrance. | Light sweet fragrance. |

Parents:

*Seed parent*.—An un-named seedling.

*Pollen parent*.—An un-named seedling.

Classification:

*Botanical classification*.—*Rosa hybrida* 'KORfre0015'.

*Commercial classification*.—Grandiflora rose.

FLOWER AND FLOWER BUD

Blooming habit: Recurrent.

Flower bud:

*Size*.—Upon opening, 25 mm in length from base of receptacle to distal end of bud and 20 mm diameter at its widest point.

*Bud form*.—Short. Globular.

*Bud color*.—As sepals first unfold, bud color is Yellow Group 10A. When ¼ open, the upper surface of petals is Yellow Group 12A, and the lower surface is Yellow Group 13B. Guard Petals are Yellow Group 11A and 11C, with intonations of Yellow-Green Group 144A and Greyed-Purple Group 184B on the midrib.

*Sepals*.—Color: Upper surface Yellow-Green Group 146C. Lower surface Yellow-Green Group 144A. Intonations of Greyed-Purple 184B. Size: Average 20 to 25 mm (l)×9 to 10 mm (w). Shape: Weak foliaceous appendages on 3 of the five sepals. Apex: Apiculate. Base: Flat at union with receptacle. Quantity: Five. Surface texture: Upper side: Strongly pubescent. Lower surface: Leathery. Margins: Entire. Stipitate glands: Limited numbers on margins.

Flower bloom:

*Fragrance*.—Strong fragrance.

*Duration*.—On the plant 14 days. As a cut flower, 10 days. Senesced petals drop away cleanly.

*Size*.—Medium for a Grandiflora rose. When open, the average flower diameter is 70 mm and the average flower height is 30 mm.

*Form*.—Shape of flower when viewed from the side: Upon opening, upper part: Flat. Upon opening, lower part: Flat. Open flower, upper part: Flat. Open flower, lower part: Concave.

Color:

*Upon opening, petals*.—Outermost petals: Outer Side: Yellow Group 13B in the basal zone, and Yellow Group 13C in the middle and marginal zones. Inner Side: Yellow Group 12A in the basal zone, and Yellow Group 12B in the middle and marginal zones. Innermost petals: Outer Side: Yellow Group 12A. Inner Side: Yellow Group 12A. No distinctive coloration at petal base observed.

*After opening, petals*.—Outermost petals: Outer Side: Yellow Group 12B in the basal zone, and Yellow Group 10C in the middle and marginal zones. Inner Side: Yellow Group 12B in the basal zone, Yellow Group 9C in the middle zone, and Yellow Group 5D in the marginal zone. Innermost petals: Outer Side: Yellow Group 9C. Inner Side: Yellow Group 9B. No distinctive coloration at petal base observed.

General tonality: On open flower Yellow Group 11A. No change in the general tonality at the end of the 4th day. Afterwards, general tonality is Yellow Group 11C.

Petals:

*Petal count*.—Very double.

*Average range*.—Approximately 120 petals under normal conditions.

*Petal reflex*.—Petals reflex somewhat.

*Petal margin*.—Entire.

*Petal shape*.—Obovate. Apex: Obtuse. Base: Cuneate.

*Petal size*.—25 to 40 mm (l)×10 to 40 mm (w).

*Petal arrangement*.—Quartered rosette.

*Texture*.—Silky.

Petaloids:

*Petaloid count*.—Average of 50 per flower.

*Petaloid size*.—7 to 20 mm (l)×5 to 15 mm (w).

*Petaloid color*.—Inner side: Yellow Group 12A. Outer side: Yellow Group 10A.

*Petaloid texture*.—Silky.

*Margins*.—Variable. Entire, undulate and highly irregular petal margins observed.

*Petaloid shape*.—Most commonly spatulate with some petaloids highly irregular. Apex: Obtuse. Base: Attenuate.

Reproductive organs:

*Pistils*.—Abundant. Approximately 100 present. Stigmas: Location: On one flower, stigmas can be found that are inferior, equal and superior in position to anthers. Color: Yellow Group 11A. Styles: Length: Variable, between 3 and 10 mm long. Color: White Group 155A.

*Stamens*.—Approximately 140 on average and regularly arranged. Anthers: Size: Average 2 mm (l)×1 mm (w). Pollen: Generally present. Color: Yellow-Orange Group 16A and Greyed-Orange Group N167A. Filaments: Color: Yellow Group 12A. Length: 5 to 7 mm.

Receptacle:

*Surface*.—Glaucous.

*Color*.—Yellow-Green Group 144B with limited intonations of Greyed-Purple 185A.

*Shape*.—Urn-shaped.

*Texture*.—Glabrous.

*Size*.—6 mm (h)×10 mm (w).

Pedicel:

*Surface*.—With few fine hairs and stipitate glands.

*Length*.—65 mm average length.

*Diameter*.—3.5 mm average diameter.

*Color*.—Yellow-Green Group 144B with strong intonations of Greyed-Red Group 182B.

*Strength*.—Strong.

*Texture*.—Papillate.

*Borne*.—Multiple flower buds per stem, generally 1 to 4. Flowers held upright.

Peduncle:

*Surface*.—Lacking fine hairs and stipitate glands.

*Length*.—55 mm average length.

*Diameter*.—3.5 mm average diameter.

*Color*.—Yellow-Green Group 144B with intonations of Greyed-Red Group 182B.

*Strength*.—Strong.

*Borne*.—Multiple flower buds per stem, generally 1 to 4. Flowers held upright.

THE PLANT

*Growth*.—Vigorous growth.

*Plant habit*.—Upright. When grown as a field plant, the average plant height is 105 cm and the average plant width is 75 cm.

*Stems*.—Stem color: Young wood: Yellow-Green Group 144A. Older wood: Yellow-Green Group 144C. Stem surface texture: Young wood: Smooth. Older wood: Smooth.

*Prickles*.—Present. Incidence: Average of 4 per each 10 cm of stem. Size: Average length: 10 mm. Color: Immature prickles: Greyed-Purple 185B. Mature prickles: Yellow Green Group 145C with intiations of Greyed Red Group 182B. Shape: Concave.

*Leaves*.—Normally 7 leaflets on normal leaves in middle of the stem. Venation pattern: Pyramidal net pattern. Leaf size: 175 to 200 mm (l)×110 to 135 mm (w). Abundance: Average.

*Leaflets*.—Size: Average size of the terminal leaflet is 65 mm (l)×45 mm (w). Shape: Elliptic. Base: Cuneate. Apex: Cuspidate. Margins: Serrated. Surface: Glossy. Texture: Upper side of leaflet: Leathery. Under side of leaflet: Leathery. Color, mature foliage: Upper Leaflet Surface: Yellow-Green Group 147A. Lower Leaflet Surface: Yellow-Green Group 147B. Color, juvenile foliage: Upper Leaflet Surface: Yellow-Green Group 146A. Lower Leaflet Surface: Yellow-Green Group 146B. Anthocyanin intonation: Greyed-Red Group 182B. Location: Covers only the most immature foliage. Arrangement: Odd pinnate. Venation: Reticulate.

*Stipules*.—Size: 30 mm (l)×12 mm (w). Stipule color: Yellow-Green Group 146A. Anthocyanin: Greyed-Red 182B, present only on stipitate glands. Stipitate glands: Abundant on margins. Margins: Pectinate. Texture: Smooth, very lightly pubescent. Shape: Apex: Apiculate. Base: Flat.

*Petiole*.—Length: Average 25 mm. Diameter: Average 2 mm. Petiole color: Yellow-Green Group 144A. Underneath: Yellow-Green Group 144B. Margins: Limited numbers of hairs and occasional stipitate glands. Prickles: None observed. Stipitate Glands: Limited numbers present on margins. Texture: Leathery.

*Petiole rachis*.—Length: Average 25 mm. Diameter: Average 2 mm. Color: Yellow-Green Group 144A. Margins: Occasional stipitate glands. Prickles: Very limited numbers underneath at leaf attachment. Stipitate glands: Limited number of stipitate glands on margins.

Hips/seed formation: None observed.

Winter hardiness: To date, the variety has been grown successfully in Zone 6.

Disease resistance: Good resistance to powdery mildew (*Sphaerotheca pannosa*) and blackspot (*Diplocarpon rosae*), diseases under normal growing conditions in Jackson County, Oreg.

I claim:

1. A new and distinct variety of rose plant, as described and illustrated herein.

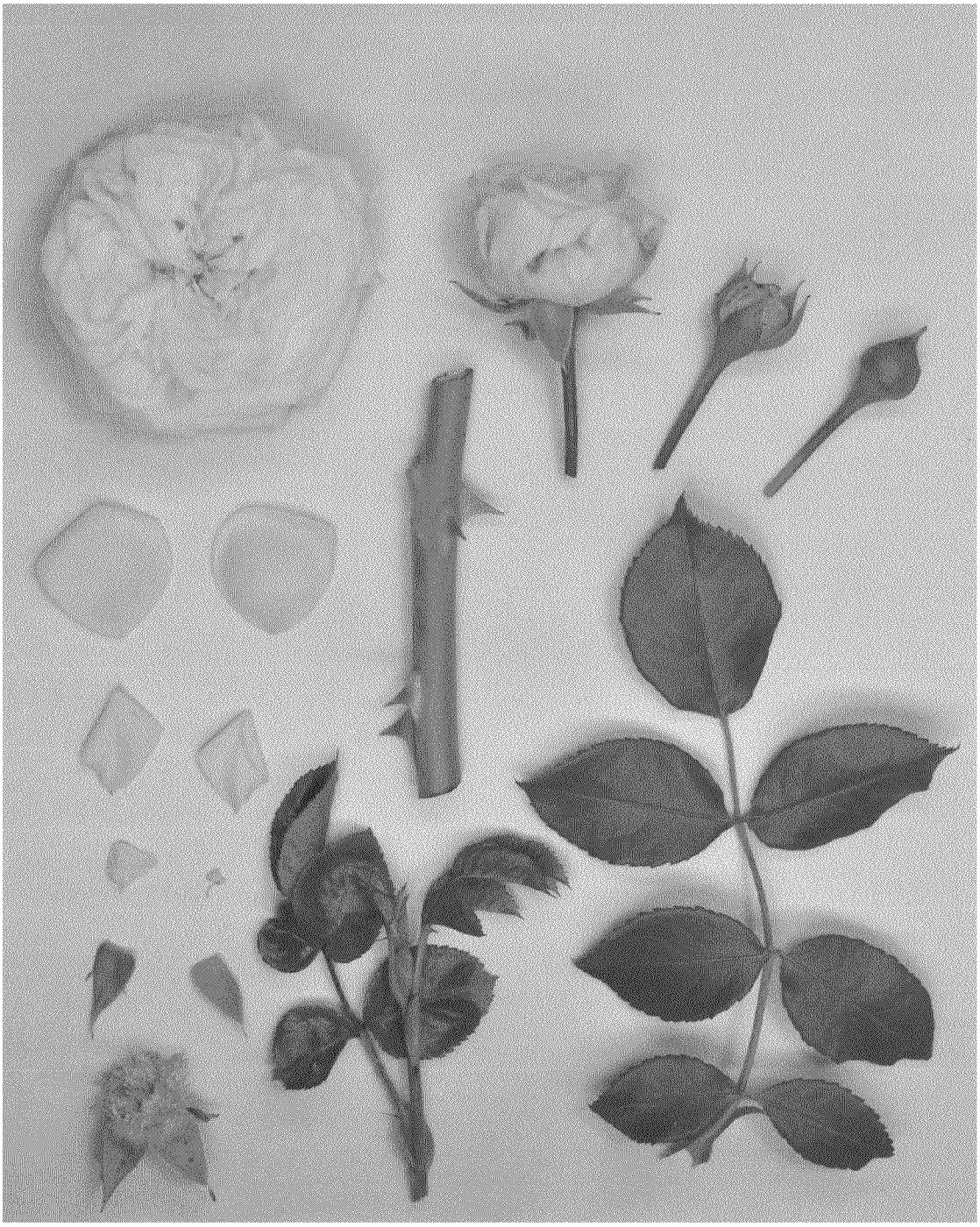

* * * * *